(12) United States Patent
Schmaier et al.

(10) Patent No.: US 6,544,750 B1
(45) Date of Patent: Apr. 8, 2003

(54) PEPTIDE ANALOGS AS SELECTIVE INHIBITORS OF THROMBIN ACTIVATION OF PROTEASE ACTIVATED RECEPTOR 1

(75) Inventors: Alvin H. Schmaier, Ann Arbor, MI (US); Ahmed A. K. Hasan, Dexter, MI (US)

(73) Assignees: Thromgen, Inc., Ann Arbor, MI (US); Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/375,808

(22) Filed: Aug. 17, 1999

(51) Int. Cl.$^7$ .............................................. G01N 33/53
(52) U.S. Cl. ................... 435/7.1; 530/350; 530/300; 514/12
(58) Field of Search ................. 530/350, 300; 435/7.1; 514/12

(56) References Cited

U.S. PATENT DOCUMENTS

| | | | | |
|---|---|---|---|---|
| 5,225,531 A | * | 7/1993 | Gresham et al. | 514/12 |
| 5,461,032 A | * | 10/1995 | Krapcho et al. | 514/12 |
| 5,472,945 A | | 12/1995 | Schmaier et al. | 514/12 |
| 5,491,086 A | | 2/1996 | Gelfand et al. | 435/194 |
| 5,589,458 A | | 12/1996 | Jameson et al. | 514/13 |
| 5,631,131 A | | 5/1997 | Jolivet et al. | 435/6 |
| 5,648,464 A | | 7/1997 | Artavanis-Tsakonas et al. | 530/350 |
| 5,747,447 A | * | 5/1998 | Swift et al. | 514/9 |
| 5,762,939 A | | 6/1998 | Smith et al. | 424/210.1 |
| 6,111,075 A | | 8/2000 | Xu et al. | |

FOREIGN PATENT DOCUMENTS

| | | | |
|---|---|---|---|
| WO | 410540 | * | 1/1991 |
| WO | WO 92/07269 | | 4/1992 |
| WO | WO96/41640 | * | 12/1996 |
| WO | WO 98/47522 | | 10/1998 |
| WO | WO 99 40214 A | | 8/1999 |

OTHER PUBLICATIONS

Alignments: Swift et al., U.S. patent No. 5,747,447, May 5, 1998.*

Silva et al., Bradykinin, A Hypotensive and Smooth Muscle Stimulating Factor Released from Plasma Globulin by Snake Venoms and Trypsin, *Amer. J. Physiol.* 156: 261 (1949).

Meloni et al., Low Molecular Weight Kininogen Binds to Platelets to Modulate Thrombin–induced Platelet Activation, *J. Biol. Chem.* 266, 6786 (1991).

Puri et al., High Molecular Weight Kininogen Inhibits Thrombin–Induced Platelet Aggregation and Cleavage of Aggregin by Inhibiting Binding of Thrombin to Platelets, *Blood* 77, 500 (1991).

Rasmussen et al., A Peptide Ligand of the Human Thrombin Receptor Antagonizes α–Thrombin and Partially Activates Platelets, *J. Biol. Chem.* 268, 14322 (1993).

Fisher et al., Muscarinic Receptor Regulation of Cytoplasmic $Ca^{2+}$ Concentrations in Human SK–N–SH Neuroblastoma Cells: $Ca^{2+}$ Requirements for Phospholipase C Activation, *Mol Pharm.* 35, 195 (1989).

Grynkiewicz et al., A New Generation of $Ca^{2+}$ Indicators with Greatly Improved Fluorescence Properties, *J. Biol. Chem.* 260, 3440 (1985).

Kitamura et al., Structural Organization of the Human Kininogen Gene and a Model for Its Evolution, *J. Biol. Chem.*, 260 8610 (1985).

Takagaki et al. Cloning and Sequence Analysis of cDNAs for Human High Molecular Weight and Low Molecular Weight Prekininogens, *J. Biol. Chem.* 260, 8601–8609 (1985).

Salveson et al., Human low–$M_r$ kininogen contains three copies of a cystatin sequence that are divergent in structure and in inhibitory activity for cysteine proteinases, *Biochem. J.* 234, 429 (1986).

Kellermann et al., Completion of the primary structure of human high–molecular–mass kininogen, *Eur. J. Biochem.* 154, 471 (1986).

Jiang et al., Domain 3 Kininogens Contains a Cell–binding Site and a Site That Modifies Thrombin Activation of Platelets, *J. Biol. Chem.* 267, 3712 (1992).

Hasan et al., Bradykinin and Its Metabolite, Arg–Pro–Pro–Gly–Phe, Are Selective Inhibitors of α–Thrombin–Induced Platelet Activation, *Circulation* 94, 517 (1996).

Tayeh et al., Surface–induced Alterations in the Kinetic Pathway for Cleavage of Human High Molecular Weight Kininogen by Plasma Kallikrein, *J. Biol. Chem.* 269, 16318 (1994).

Vu et al., Molecular Cloning of a Functional Thrombin Receptor Reveals a Novel Proteolytic Mechanism of Receptor Activation. *Cell* 64, 1057 (1991).

Brass et al., Structure and Function of the Human Platelet Thrombin Receptor, *J. Biol. Chem.* 267, 13795 (1992).

(List continued on next page.)

Primary Examiner—Karen Cochrane Carlson
Assistant Examiner—Hope A. Robinson
(74) Attorney, Agent, or Firm—Venable; Keith G. Haddaway; Julie A. Petruzzelli

(57) ABSTRACT

The invention relates to inhibiting human platelet aggregation, thrombosis and cell activation mediated by PAR1 with peptide analogs corresponding to those of Formula I and II, wherein Formula I is:

Arg-Gly-Lys-$Z_4$-Cys wherein:

$Z_4$ is any naturally occurring amino acid, excluding cysteine; and wherein Formula II is:

Arg-Gly-Asp-$Z_4$-Cys wherein:

$Z_4$ is any naturally occurring amino acid, excluding cysteine.

33 Claims, 9 Drawing Sheets

OTHER PUBLICATIONS

Hasan et al., Thrombostatin Inhibits Induced Canine Coronary Thrombosis, *Thromb. Haemost.*, 1182 (1999).

Houghten et al., Generation and use of synthetic peptide combinatorial libraries for basic research and drug discovery, *Nature*, 354, 84 (1991).

Dooley et al., An All D–Amino Acid Opioid Peptide with Central Analgesic Activity from a Combinatorial Library, *Science* 266, 2019 (1994).

Gisin, The monitoring of reactions in solid–phase peptide synthesis with picric acid, *Analytica chim. Acta.* 58, 248 (1972).

Kaiser et al., Color Test for Detection of Free Terminal Amino Groups in the Solid–Phase Synthesis of Peptides, *Analyt Biochem.* 34, 595 (1970).

Cuervo et al., The Magainins: Sequence Factors to Increased Antimicrobial Activity and Decreased Hemolytic Activity, *Peptide Res.* 1, 81 (1988).

Tam. J.P., et al., SN2 Deprotection of Synthetic Peptides with a Low Concentration of HF in Dimethyl Sulfide: Evidence and Application in Peptide Synthesis, *J. Am. Chem. Soc.* 105, 6442 (1983).

Hynes, Integrins: Versatility, Modulation, and Signaling in Cell Adhesion, *Cell*, 69, 11 (1992).

Parise et al., Synthetic Peptides Derived from Fibrinogen and Fibronectin Change the Conformation of Purified Platelet Glycoprotein IIb–IIIa, *J. Biol. Chem.*, 262, 12597 (1987).

Pierschbacher et al., Influence of Stereochemistry of the Sequence Arg–Gly–Asp–Xaa on Binding Specificity in Cell Adhesion, *J. Biol. Chem.* 262, 17294 (1987).

Houghthen et al., The Use of Synthetic Peptide Combinatorial Libraries for the Identification of Bioactive Peptides, BioTechniques 13, 412 (1992).

Houghten et al., Simplified procedure for carrying out simultaneous multiple hydrogen fluoride cleavages of protected peptide resins, *Int. J. Peptide Protein Res.* 27, 673–678 (1986).

Croce, Kevin, "Inhibition of Calpain Blocks Platelet Secretion, Aggregation, and Spreading," *Biological Chemistry*, vol. 274, No. 51, Issue of Dec. 17, pp. 36321–36327 (1999).

Wang et al., (Abstract) "An efficient Procedure for Cleavage of t–butyl Protected Crysteine in Soli Phase Peptide Synthesis", Chemical Abstracts Service.

Pedicord et al., (Abstract) "Glycoprotein IIb/IIIa Receptor Antagonists Inhibit the Development of Platelet Procoagulant Activity", Chemical Abstracts Service.

* cited by examiner

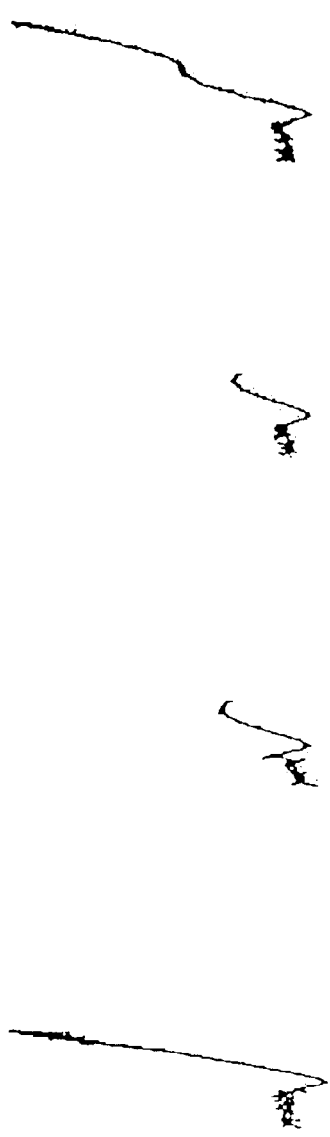

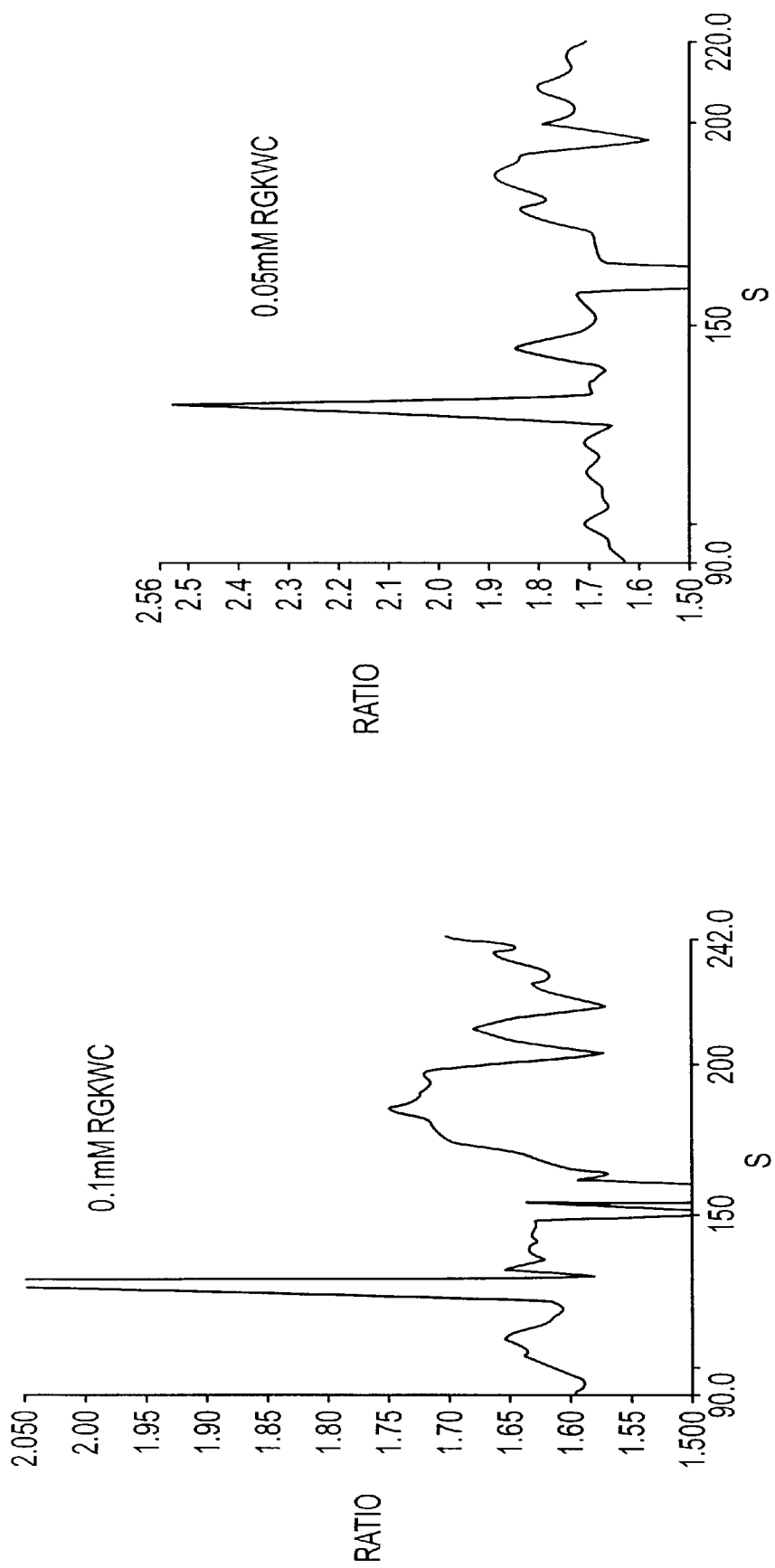

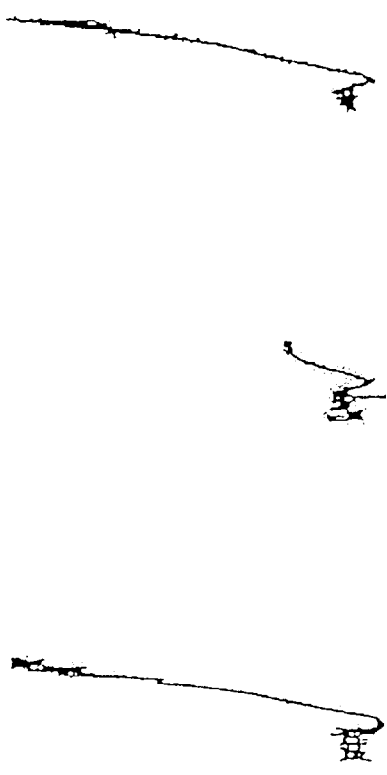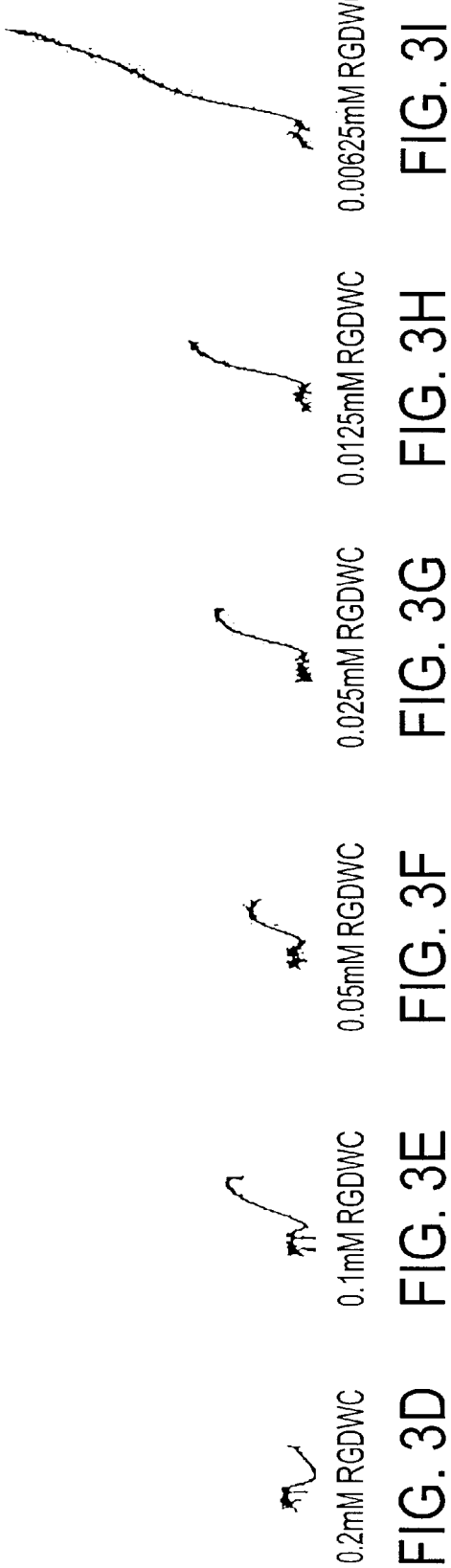

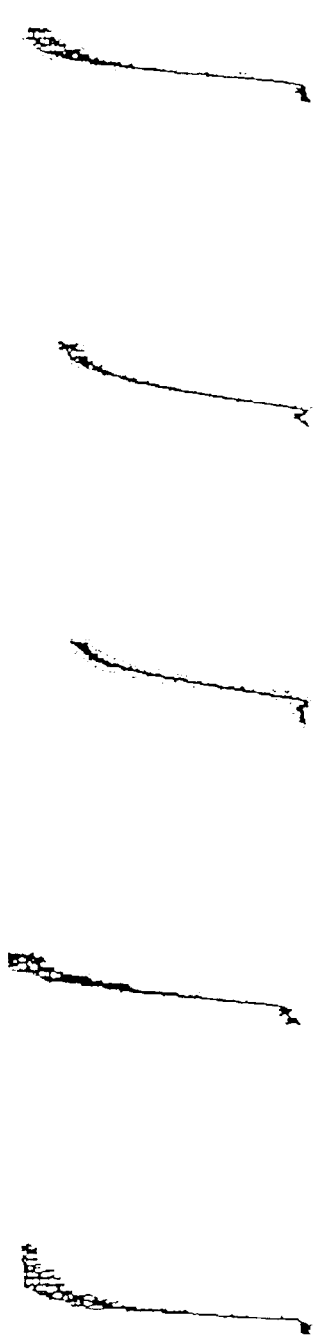
FIG. 5A 4.5μM ADP
FIG. 5B 1mM RPPGF
FIG. 5C 1mM MaP₄
FIG. 5D 0.5mM MaP₄
FIG. 5E 1mM RGKWC
FIG. 5F 1mM RGDWC
FIG. 5G 0.5mM RGDWC
FIG. 5H 0.25mM RGDWC
FIG. 5I 0.125mM RGDWC
FIG. 5J 0.0625mM RGDWC

PEPTIDE ANALOGS AS SELECTIVE INHIBITORS OF THROMBIN ACTIVATION OF PROTEASE ACTIVATED RECEPTOR 1

REFERENCE TO GOVERNMENT GRANT

The invention described herein was made, in part, in the course of work supported by the National Heart Lung and Blood Institute under Grant Nos. HL55907 and 61081. The government has certain rights in the invention.

FIELD OF INVENTION

This invention relates to the inhibition of α- and γ-thrombin-induced cell activation.

BACKGROUND OF THE INVENTION

Bradykinin (Arg-Pro-Pro-Gly-Phe-Ser-Pro-Phe-Arg, SEQ ID NO: 40) is a vasoactive peptide released from the precursor plasma kininogens by plasma and tissue kallikreins and other enzymes (Silva et al., *Amer. J. Physiol.* 156: 26–274 (1949)). The parent proteins of bradykinin, high (HK) and low (LK) molecular weight. kininogens were recognized to have the ability to inhibit α- and γ-thrombin-induced platelet activation (Meloni et al., *J. Biol. Chem.* 266, 6786 (1991); Puri et al., *Blood* 77, 500 (1991)). Both low and high molecular weight kininogens have identical amino acid sequences from their amino-terminus through 12 amino acids beyond the carboxy-terminus of bradykinin. Both LK and HK share a common heavy chain (62 kDa), the bradykinin (BK) moiety (0.9 kDa), and the first 12 amino acids of the amino terminal portion of each of their "light chains" (Takagaki et al., *J. Biol. Chem.* 260, 8601–8609 (1985); Kitamura et al., *J. Biol. Chem.*, 260, 8610–8617 (1985)). This identity corresponds to residues 1 through about residue 383. See Salveson et al., *Biochem J.* 243, 429 (1986); Kellerman et al., *Eur. J. Biochem.* 154, 471 (1986). The HK and LK kininogens diverge in the size of their light chains; the light chain of LK is 4 kDa; that of HK is 56 kDa. (Takagaki et al., supra; Kitamura et al., supra.). The kininogens prevent thrombin-induced platelet activation without inhibiting thrombin's ability to hydrolyze a chromogenic substrate. Full-length kininogens prevent thrombin from binding to platelets. They do not interfere with thrombin's ability to proteolyze, i.e. cleave fibrinogen, which allows released fibrin monomer to make a fibrin clot. Thus, the prior art indicated that the kininogens' ability to inhibit thrombin activation of platelets was not due to their direct interaction with the thrombin molecule itself (Meloni et al., supra; Puri et al., supra).

The thrombin inhibitory activity of the kininogens appeared to be localized to an isolated domain 3 of the kininogens' heavy chain, because domain 3 retained all the thrombin inhibitory activity of the whole protein (Jiang et al., *J. Biol. Chem.* 267, 3712 (1992)). The thrombin inhibitory activity of the kininogens was later found to be associated with domain 4, the bradykinin sequence,: which was attached to the carboxyterminal end of isolated domain 3 prepared by proteolytic cleavage of whole LK (Hasan et al., *Circulation* 94, 517–528 (1996); Tayeh et al., *J. Biol. Chem.* 269, 16318–16325 (1994)). The thrombin inhibitory region of domain 4, the bradykinin sequence, demonstrated a number of features. This sequence did not prevent thrombin from binding to platelets and it did not prevent the thrombin receptor activation peptide (TRAP), SFLLRN (SEQ ID NO: 46), from stimulating calcium mobilization and platelet aggregation in platelets. This sequence from domain 4 prevented thrombin-activated platelets from losing an epitope to monoclonal antibody SPAN12. Monoclonal antibody SPAN12 is directed to the thrombin cleavage site on protease activated receptor 1 (PAR1) (Hasan et al., supra; Vu et al., *Cell* 64, 1057–1068 (1991); Brass et al., *J. Biol. Chem.* 267, 13795–13798 (1992)). Monoclonal antibody SPAN12 was raised to the peptide NATLDPRSFLLR (Asn-Ala-Thr-Leu-Asp-Pro-Arg-Ser-Phe-Leu-Leu-Arg, SEQ ID NO: 41) (Brass et. al., supra.). Further, bradykinin analog peptides prevented α-thrombin from cleaving the peptide, NATLD-PRSFLLR (Asn-Ala-Thr-Leu-Asp-Pro-Arg-Ser-Phe-Leu-Leu-Arg, SEQ ID NO: 41), between arginine and serine, the identical place on PAR1 that thrombin cleaves to activate this receptor. Although there are a number of peptide analogs of bradykinin that demonstrated thrombin inhibiting activity against platelet activation, the minimal sequences retaining this activity are the peptides, RPPGF (Arg-Pro-Pro-Gly-Phe, SEQ ID NO: 39), RPPG (Arg-Pro-Pro-Gly, SEQ ID NO: 45), and RPP (Arg-Pro-Pro). More recent investigations indicated that FITC-labeled (fluorescein isothiocyanate RPPGF (Arg-Pro-Pro-Gly-Phe, SEQ ID NO: 39) has the ability to directly bind to platelets (Hasan et al., *Thromb Haemost.* In Press, (1999)). These data indicated that the RPPGF (SEQ ID NO: 39) and related bradykinin analog peptides have the ability to bind to platelets to prevent thrombin-induced platelet activation.

The present invention relates to inhibition of thrombin-induced activation in human cells. Inhibition of thrombin activation of platelets can be either through an inhibitor of thrombin directed to the thrombin molecule itself or an inhibitor directed to substrates of thrombin. Protease activated receptor 1 (PAR1) is a specific substrate of thrombin to which this class of inhibitor is directed. The present invention is directed to inhibition of this thrombin substrate on any cell that expresses PAR1. These cells include platelets, endothelial cells, smooth muscle cells, fibroblasts, neuronal cells, or any other cell that contains this receptor. The present invention does not address inhibition of ADP-induced platelet activation as related to the thienopyridines class of agents, ticlopidine and clopidogrel. Similarly, the present invention does not address inhibition of platelet aggregation to the formation of the heterodimeric complex of platelet glycoprotein IIb/IIIa (i.e. integrin $\alpha_{IIb}\beta_3$). These compounds include the human-mouse chimeric monoclonal antibody 7E3c (ReoPro, abciximab), eptifibatide (Integrilin), and tirofiban (Aggrastat). This invention does not address aspirin inhibition of platelet activation by inhibition of platelet cyclooxygenase.

The following abbreviations have been used:

BK: bradykinin (SEQ ID NO: 40);

D3: domain 3 of kininogens;

D4: domain 4 of kininogen that is the bradykinin region;

FITC: fluorescein isothiocyanate;

HK: high molecular weight kininogen;

LK: low molecular weight kininogen;

MAP4RPPGF: A four-branched peptide consisting of a β-alanine core with a single lysine attached at its amino terminal end followed by two additional lysines. Each lysine will then have two RPPGF (Arg-Pro-Pro-Gly-Phe, SEQ ID NO: 39) peptides attached by the phenylalanine to each of the lysines;

NAT12: peptide sequence Asn-Ala-Thr-Leu-Asp-Pro-Arg-Ser-Phe-Leu-Leu-Arg (SEQ ID NO: 41) that spans the ct-thrombin cleavage site on the thrombin receptor;

PAR1: protease activated receptor 1;

PTCA: percutaneous transluminal coronary angioplasty;

RPPGF: Arg-Pro-Pro-Gly-Phe (SEQ ID NO: 39);
RPPG: Arg-Pro-Pro-Gly (SEQ ID NO: 45);
RPP: Arg-Pro-Pro;
SPAN12: a monoclonal antibody specific for the sequence Asn-Ala-Thr-Leu-Asp-Pro-Arg-Ser-Phe-Leu-Leu-Arg (SEQ ID NO: 41) that spans the α-thrombin cleavage site on the thrombin receptor; and
Z: nomenclature for any naturally occurring amino acid.

SUMMARY OF THE INVENTION

The invention relates to a series of compounds to inhibit thrombin-induced platelet or human cell activation upon administering an effective amount of a peptide that inhibits thrombin activation of platelets or human cells, wherein said peptide has an amino acid sequence of the formula:

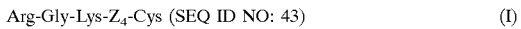
Arg-Gly-Lys-$Z_4$-Cys (SEQ ID NO: 43)   (I)

wherein:

$Z_4$ is any naturally occurring amino acid, excluding cysteine.

The invention also comprises a series of compounds to inhibit thrombin-induced platelet or human cell activation upon administering an effective amount of a peptide that inhibits thrombin activation of platelets or human cells, wherein said peptide has an amino acid sequence of the formula:

Arg-Gly-Asp-$Z_4$-Cys (SEQ ID NO: 44)   (II)

wherein:

$Z_4$ is any naturally occurring amino acid, excluding cysteine.

The twenty amino acids (followed by their three letter abbreviations and one letter symbol) are set forth in TABLE VII below.

One embodiment of the invention comprises treating platelets or human cells with a compound of Formula I or Formula II to inhibit thrombin activation of platelets or activation of other cells, which express the thrombin receptor. Some of the preferred analogs include RGKWC, RGKKC, RGKLC, RGKTC, RGKRC, RGDWC, RGDFC, RGDEC, and RGDNC (SEQ ID NO's 5, 14, 1, 2, 3, 20, 21, 22 & 32, respectively).

An object of administration of these peptides of Formulae I and II to cells is to prevent thrombosis, i.e., an occlusion of a vessel due to formation of a platelet-rich, fibrin-rich or a mixed platelet-fibrin thrombus. Accordingly, the invention relates to the foregoing analogs, and to the contact of these analogs with platelets and human cells which express the thrombin receptor to prevent thrombosis.

DESCRIPTION OF THE FIGURES

FIG. 1 illustrates the effect of the peptide RGKWC (Arg-Gly-Lys-Trp-Cys, SEQ ID NO: 5) on γ-thrombin-induced platelet aggregation in platelet-rich plasma. The figure shows aggregation tracings. In the upper left, 70 nM γ-thrombin induced a full aggregation. One mM RPPGF (Arg-Pro-Pro-Gly-Phe, SEQ ID NO: 39), a control aggregation, abolished thrombin-induced platelet aggregation. Aggregation returned at 0.25 mM RPPGF (SEQ ID NO: 39). In comparison, 1 mM RGKWC (Arg-Gly-Lys-Trp-Cys, SEQ ID NO: 5) also abolished γ-thrombin-induced platelet aggregation. At 0.125 mM RGKWC (SEQ ID NO: 5), thrombin-induced platelet aggregation returned.

FIG. 3 illustrates the effect of the peptide RGDWC (Arg-Gly-Asp-Trp-Cys, SEQ ID NO: 20) on γ-thrombin-induced platelet aggregation. Seventy nM γ-thrombin induced a full level of platelet aggregation. One mM RPPGF (Arg-Pro-Pro-Gly-Phe, SEQ ID NO: 39) completely abolished γ-thrombin-induced platelet aggregation. RGDWC (Arg-Gly-Asp-Trp-Cys, SEQ ID NO: 20) (0.2 mM) completely abolished γ-thrombin-induced platelet aggregation. At 6.25 μM RGDWC (SEQ ID NO: 20), γ-thrombin-induced platelet aggregation returned.

FIG. 5 illustrates the effect on ADP-induced platelet aggregation of various peptides that interfere with thrombin-induced platelet aggregation. Four and a half μM ADP induced a full aggregation response. Peptides RPPGF (Arg-Pro-Pro-Gly-Phe, SEQ ID NO: 39), MAP4RPPGF, and RGKWC (Arg-Gly-Lys-Trp-Cys, SEQ ID NO: 5) at 1 mM did not inhibit ADP-induced platelet aggregation. Alternatively, RGDWC (Arg-Gly-Asp-Trp-Cys, SEQ ID NO: 20) at 0.5 mM abolished ADP-induced platelet aggregation.

Figure 2B:
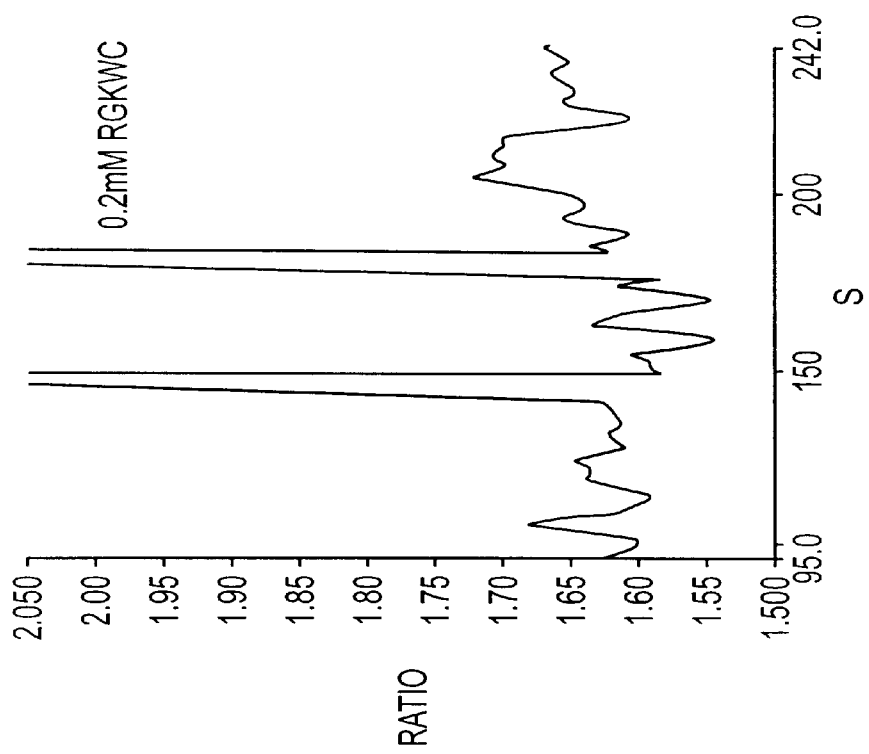
FIG. 2 illustrates the effect of the peptide RGKWC (Arg-Gly-Lys-Trp-Cys, SEQ ID NO: 5) on γ-thrombin-induced calcium mobilization in fibroblasts. In the upper left, 2 nM α-thrombin induces a robust level of $Ca^{2+}$ mobilization in these fibroblasts. Using RGKWC (SEQ ID NO: 5) at 0.2 mM, α-thrombin-induced calcium mobilization is abolished. As the concentration of RGKWC (SEQ ID NO: 5) decreased, the ability of thrombin to induce Ca2+ mobilization returned. At 12.5 μM RGKWC (SEQ ID NO: 5), α-thrombin overcame the inhibitory effect of the peptide.

Table I is a tabulation of the $RGKO_4C$ (SEQ ID NO: 43) sublibrary and the influence of each peptide on γ-thrombin-induced platelet aggregation in platelet-rich plasma. The numbers in the column under "Fold Increase in Aggregation Inhibition Over RPPGF" (SEQ ID NO: 39) represent the increase in the degree of inhibition of thrombin-induced platelet aggregation as compared to RPPGF (SEQ ID NO: 39) at 0.2 mM.

Table II is a tabulation of the $RGKO_4C$ (SEQ ID NO: 43) sublibrary and the influence of each peptide on γ-thrombin-induced calcium mobilization in fibroblasts. The numbers in the column under "$Ca^{2+}$% Inhibition" represent the degree of inhibition of thrombin-induced calcium mobilization by the peptide.

Table III is a tabulation of the $RGKO_4C$ (SEQ ID NO: 43) sublibrary and the affinity of biotin-NAT12 to bind to each of the peptides coupled to microtiter plate wells. The numbers in the column under "Level of Binding to Biotin-NAT12" represent the increased degree of binding of biotin-NAT12 to the peptide listed as compared to RPPGF (SEQ ID NO: 39), the latter of which is given an arbitrary binding level of 1.

Table IV is a tabulation of the $RGDO_4C$ (SEQ ID NO: 44) sublibrary and the influence of each peptide on γ-thrombininduced platelet aggregation. The numbers in the column under "Fold Increase in Aggregation Inhibition Over (SEQ ID NO: 39) RPPGF" represent the increase in the degree of inhibition of thrombin-induced platelet aggregation as compared to RPPGF (SEQ ID NO: 39) at 0.2 mM.

Table V is a tabulation of the $RGDO_4C$ (SEQ ID NO: 44) sublibrary and the influence of each peptide on γ-thrombin-induced calcium mobilization in fibroblasts. The numbers in the column under "$Ca^{2+}$% Inhibition" represent the degree of inhibition of thrombin-induced calcium mobilization by the peptide.

Table VI is a tabulation of the $RGDO_4C$ (SEQ ID NO: 44) sublibrary and the affinity of biotin-NAT12 to bind to each of the peptides coupled to microtiter plate wells. The numbers in the column under "Level of Binding to Biotin-NAT12" represent the increased degree of binding of biotin-NAT12 to the peptide listed than to RPPGF (SEQ ID NO: 39), the latter of which is given an arbitrary binding level of I.

DETAILED DESCRIPTION OF THE INVENTION

The invention relates to the peptide analogs of Formulae I and II above. Peptides of the invention are produced by conventional solid phase peptide synthesis techniques using automated synthesis. Each reference cited herein is incorporated by reference as if each were individually incorporated by reference The segments of interest may also be prepared by recombinant DNA techniques. Accordingly, the method of the present invention can be implemented with polypeptides prepared by peptide synthetic methods or by recombinant techniques.

In accordance with the present invention naturally occurring or synthetic amino acids having the general formula $^{31}CO_2(RCHCH(NH_3)+$ are produced by addition of the group to either the carboxyl or amino terminus of a peptide comprising the core sequence in order to form chain expansion analogs. The peptides of Formula I and Formula II comprise at most ten (10) amino acids in sequence. Preferably, the peptide compound and the segment comprise five amino acids in sequence. In accordance with the preferred synthesis, the synthetic peptide combinatorial libraries (SPCL) of $H-R-O_2-X-X-C-NH_2$, $H-R-X-O_3-X-C-NH_2$, $H-R-X-X-O_4-C-NH_2$, $H-R-G-O_3-X-C-NH_2$, and $H-R-G-X-O_4-C-NH2$, in positional scanning format and $H-R-G-K-O_4-C-NH_2$ and $H-R-G-D-O_4-C-NH_2$ (SEQ ID NOS 43 & 44, respectively) in iterative format were synthesized according to the published method (Houghten et al., *BioTechniques* 13(3): 412–421(1992). $O_2$, $O_3$, and $O_4$ are the defined positions in which one of any naturally occurring amino acid, except cysteine, is placed. The cysteine was excluded to prevent dimer or oligomer formation. "X" represents the equimolar mixture (Houghten et al., *BioTechniques* 13(3): 412–421(1992)) of the naturally occurring amino acids, except cysteine. Here again, cysteine was omitted to avoid dimerization or oligomerization.

The first positional scanning library was composed of three sublibraries ($H-R-O_2-X-X-C-NH_2$, $H-R-X-O_3-X-C-NH_2$, and $H-R-X-X-O_4-C-NH_2$), each composed of 19 separate peptide mixtures, which represent a total of $19^3$ or 6859 individual peptides. Each sublibrary contained the same individual sequence but grouped in a different way. The screening of the first library, i.e., all three first sublibraries, provided the information about the most effective amino acid at each position and the relative specificity of each position. From the screening data using the three assays (the platelet aggregation assay, the calcium mobilization assay and the biotin-NAT12 binding assay) described more fully within, it appeared that glycine (G) at the second position conferred the most specific inhibitory activity (i.e. no other amino acids were found to be as active as glycine at this position). There was no clear specific amino acid candidate for the third or fourth position.

With this information, a second library was synthesized in positional scanning format having the first and second position defined as arginine (R) and glycine (G), respectively. The second library was synthesized following the same method of the SPCL synthesis referenced above. This second library was composed of two sublibraries ($H-R-G-O_3-X-C-NH_2$ and $H-R-G-X-O_4-C-NH_2$), each composed of 19 separate peptide mixtures, which represented a total of $19^2$ or 361 individual peptides. Again, $O_3$, $O_4$, and X are used as described above for the first library. Screening these two sublibraries revealed that two amino acids, lysine (K) and aspartic acid (D) were most active and relatively specific residues for the third position after arginine and glycine. There was no clear candidate residue for the fourth position. In order to determine the fourth positional moiety, a third library was synthesized in iterative format according to published methods. (Houghton, et al., *BioTechniques* 13(3): 412–421 (1992)). This library was composed of two sublibraries: $H-R-G-K-O_4-C-NH_2$ and $H-R-G-D-O_4-C-NH_2$, (SEQ ID NOS 43 and 44). Each library consisted of 19 individual peptides with a total of 38 individual peptides. The $O_4$ was replaced with each natural amino acid, except cysteine.

This invention is directed to a method for preventing thrombosis using peptide analogs that act as selective antithrombins. These peptide analogs are selective antithrombins because they are able to inhibit human α-thrombin and γ-thrombin from activating platelets or other cells by cleaving PAR1 at or near its thrombin cleavage site to prevent thrombin induced stimulus-response coupling and activation of platelets and other cells. The relative concentrations of thrombin to platelets used to induce platelet activation or aggregation ranged from about 0.05 to about 3 nM of α-thrombin or about 15 to about 70 nM of γ-thrombin. Compounds of Formula I and Formula II are a first generation of compounds that achieve selectivity in inhibiting thrombin activation by being directed to a substrate of thrombin rather than the enzyme itself. Most known thrombin inhibitors, hirudin, hirulog, hirugin, argatroban, etc., interfere with α-thrombin's action by blocking all of its proteolytic activity. Use of these known proteolytic inhibitors to block α-thrombin activation of platelets and other cells expressing PAR1 may result in excessive anticoagulation, hemorrhage, and interference with other important biologic activities such as mitogenesis and cell proliferation. The peptide analogs utilized in the present method allow for inhibition of thrombin induced platelet or other cell stimulus-response coupling and activation mediated by one substrate of thrombin, PAR1, without interfering with other α-thrombin activities such as activation of factors V and XIII.

We have found that the peptides described herein inhibit thrombin cleavage of the thrombin receptor (PAR1) which is expressed on platelets, fibroblasts and other human cells. Thus, we have found that the peptides described here have the ability to inhibit thrombin-induced platelet activation by blocking cleavage of PAR1 and subsequent activation of platelets by exposure of the new amino terminus of the cleaved receptor. Administration of a peptide analog described herein comprises a method for inhibiting thrombin-induced activation of platelets, endothelial cells, brain cells, fibroblasts, smooth muscle cells, or other cells that contain the PAR1 receptor for thrombin. This function inhibits platelet thrombus formation and other activities mediated by the thrombin receptor.

The peptide analogs described here do not inhibit platelet activation by the same mechanism as intact kininogens or isolated domain 3. One mM peptide analogs do not block $^{125}$I-α-thrombin binding to platelets, as do molar excess purified HK, LK, or isolated domain 3. We have found that these peptide analogs:

1) block α-thrombin-induced calcium mobilization in fibroblasts;
2) block γ-thrombin-induced platelet aggregation; and
3) directly bind biotin-NAT12.

According to one embodiment of the invention, these peptide analogs represent an amino acid substitution in the fourth position of the parent peptide that has the sequence RGKZ$_4$C (Arg-Gly-Lys-Z$_4$-Cys) (SEQ ID NO: 43). The fourth position can be any naturally occurring amino acid, except cysteine. In a further embodiment of the invention, these peptide analogs represent an amino acid substitution in the fourth position of the parent peptide that have the sequence RGDZ$_4$C (Arg-Gly-Asp-Z$_4$-Cys, SEQ ID NO: 44). The fourth position can be any naturally occurring amino acid, except cysteine.

I. Preparation of Peptide Analogs that Intefere with Thrombin-Induced Platelet Aggregation A. Assays to Screen Combinatorial Libraries Three assays were developed to screen peptides produced by combinatorial libraries:

1. Platelet Aggregation

Fresh whole blood was collected and mixed with 0.013 M sodium citrate and platelet-rich plasma was prepared according to the method of Meloni et al., *J. Biol. Chem.* 266, 6786 (1991). Platelet-rich plasma with a normalized platelet count between 2–2.5×10$^8$ platelets/ml was added to a cuvette of an aggregometer (Chronlog Corp., Havertown, Pa.), standardized using the protocol of Meloni et al., supra. Peptides to be examined were added to the cuvette and the mixture stabilized for a few moments. Once the baseline was stabilized, γ-thrombin (10–70 NM) (Haematologic Technologies, Essex Junction, Vt.) was added to determine the minimal concentration of the agonist necessary to achieve full platelet aggregation. All investigations with peptides were performed using threshold concentrations of γ-thrombin. Aggregation was allowed to proceed for 5 minutes before stopping. When ADP-induced platelet aggregation studies were performed, 1–5 μM ADP (Sigrna) was added to the cuvette containing platelet-rich plasma.

As shown in FIG. 1, 70 nM γ-thrombin induced a full platelet aggregatory response. The aggregation response was abolished by 0.5–1 mM (SEQ ID NO: 39) RPPGF. At 0.25 mM RPPGF (SEQ ID NO: 39), γ-thrombin-induced platelet aggregation returned. This inhibitory response was compared to that seen with RGKWC (SEQ ID NO: 5). At 0.25–1 mM RGKWC (SEQ ID NO: 5), γ-thrombin-induced platelet aggregation was completely inhibited. At 0.125 mM RGKWC (SEQ ID NO: 5), γ- thrombin-induced platelet aggregation returned to levels seen without any inhibitor. Table I shows a list of RGKO$_4$C (SEQ ID NO: 43) peptides which inhibit γ-thrombin-induced platelet aggregation. The most potent to least potent inhibitors of γ-thrombin-induced platelet aggregation are RGKLC, RGKTC, RGKRC, RGKIC, RGKWC, RGKYC, and RGKMC (SEQ ID NOS 1–7, respectively) in decreasing order.

FIG. 3 shows results with the RGDWC (SEQ ID NO: 20) peptide on γ-thrombin-induced platelet aggregation. Seventy nM γ-thrombin induced threshold platelet aggregation. One mM RPPGF (SEQ ID NO: 39) abolished γ-thrombin-induced platelet aggregation. Peptide RGDWC (SEQ ID NO: 20) inhibited γ-thrombin-induced platelet aggregation down to a concentration of 25 μM. At 6.25 μM RGDWC (SEQ ID NO: 20), γ-thrombin-induced platelet aggregation returned to normnal. Table IV lists all the RGDO$_4$C (SEQ ID NO: 44) peptides from most potent to weakest that inhibit γ-thrombin-induced platelet aggregation.

FIG. 5 compares the ability of RGKWC (SEQ ID NO: 5) and RGDWC (SEQ ID NO: 20) peptides on ADP-induced platelet aggregation. Untreated platelets had full platelet aggregation with 4.5 μM ADP. One mM RPPGF (SEQ ID NO: 39), MAP4RPPGF (MaP$_4$), and RGKWC (SEQ ID NO: 5) did not inhibit ADP-induced platelet aggregation. Alternatively, RGDWC (SEQ ID NO: 20) at ≧0.5 mM completely inhibited ADP-induced platelet aggregation. These data indicated that the RGKO$_4$C (SEQ ID NO: 43) group of compounds was more specifically directed to thrombin-induced platelet aggregation than the RGDO$_4$C (SEQ ID NO: 44) group of compounds which could be influencing thrombin-induced platelet aggregation, but also were influencing ADP-induced platelet aggregation. It is believed that the RGD-based compounds partially inhibit thrombin-induced platelet aggregation by blocking the final common pathway of platelet aggregation, i.e., the binding of fibrinogen to the heterodimeric complex of glycoprotein IIb/IIIa, ie., α$_{IIb}$β$_3$ integrin.

2. Calcium Mobilization Assay

Figure 2A:
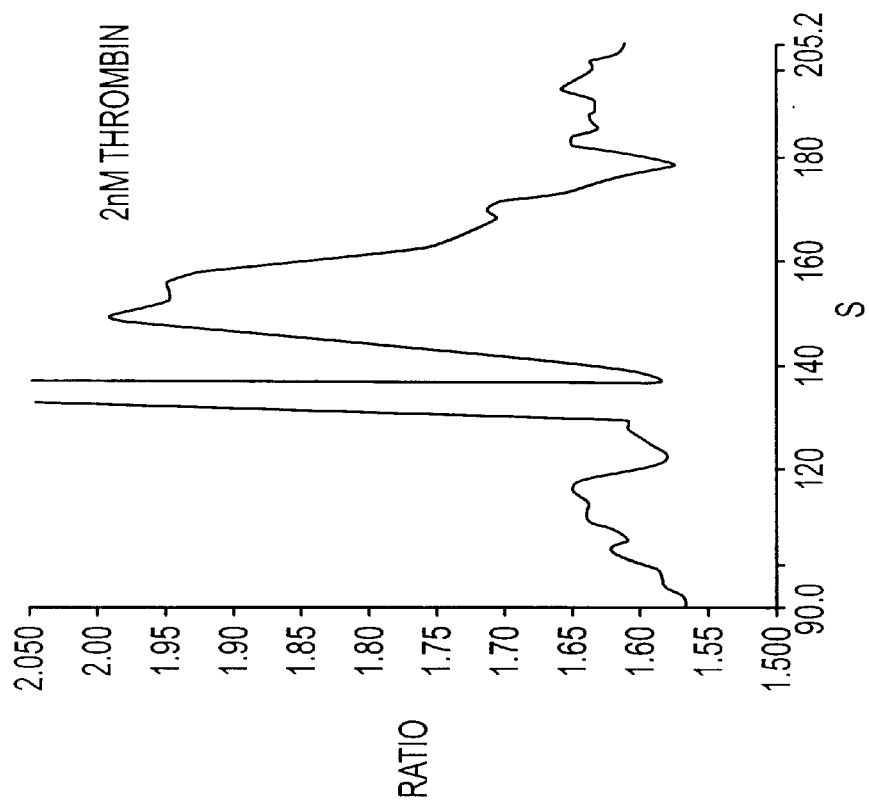
Figure 2F:
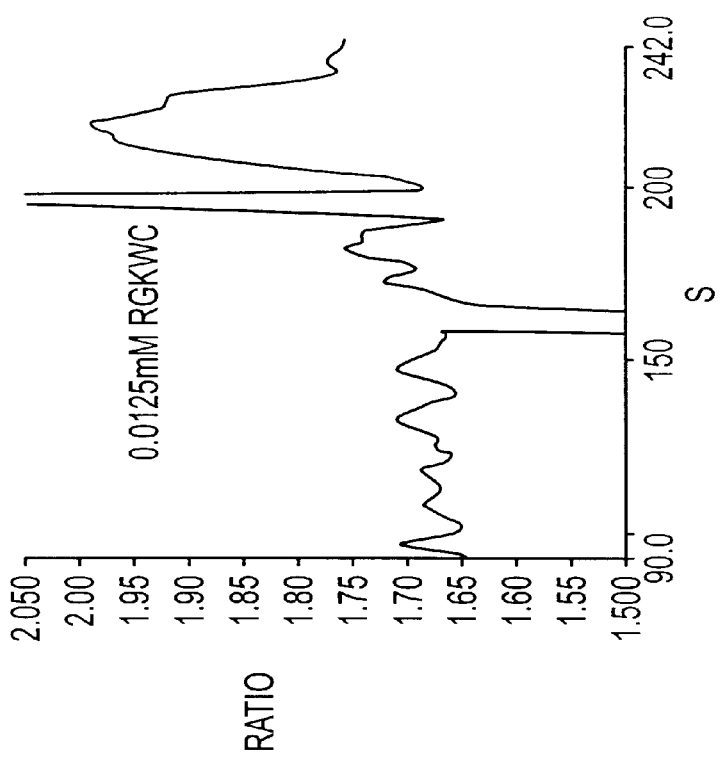
Figure 2E:
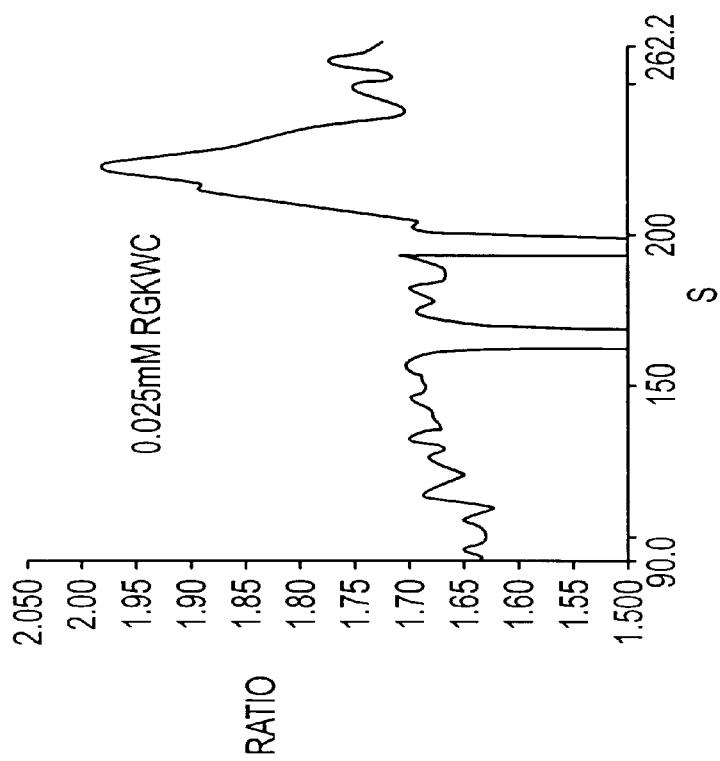
Figure 4A:
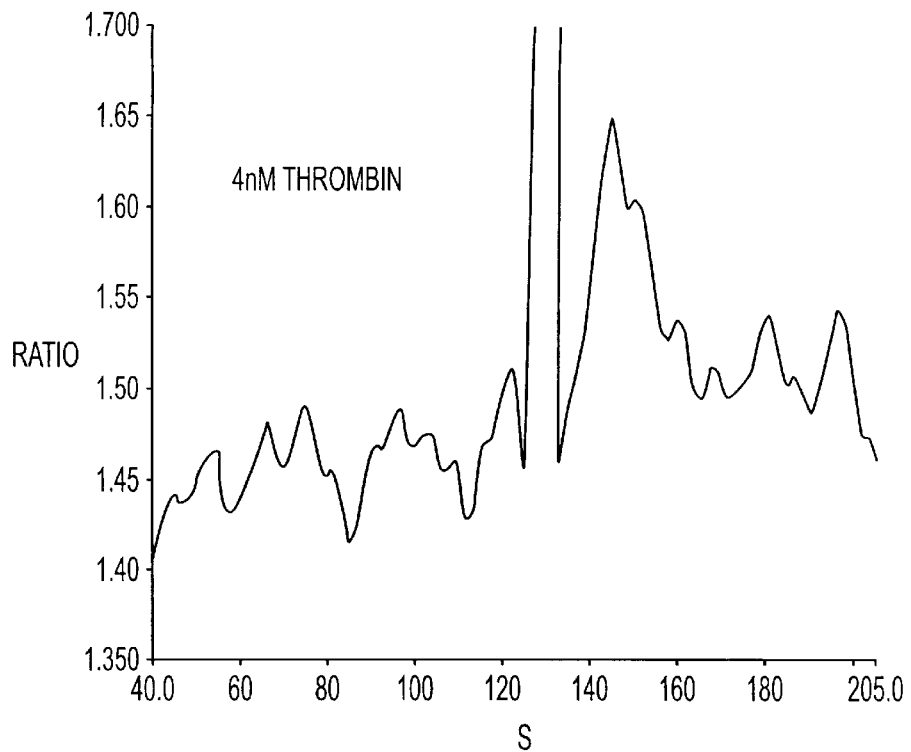
FIG. 4 illustrates the effect of RGDWC (Arg-Gly-Asp-Trp-Cys, SEQ ID NO: 20) on α-thrombin-induced $Ca^{2+}$ mobilization. Four nM α-thrombin induced a full $Ca^{2+}$ mobilization. RGDWC (SEQ ID NO: 20) at 0.2 mM almost had no effect on thrombin-induced $Ca^{2+}$ mobilization.
Figure 4B:
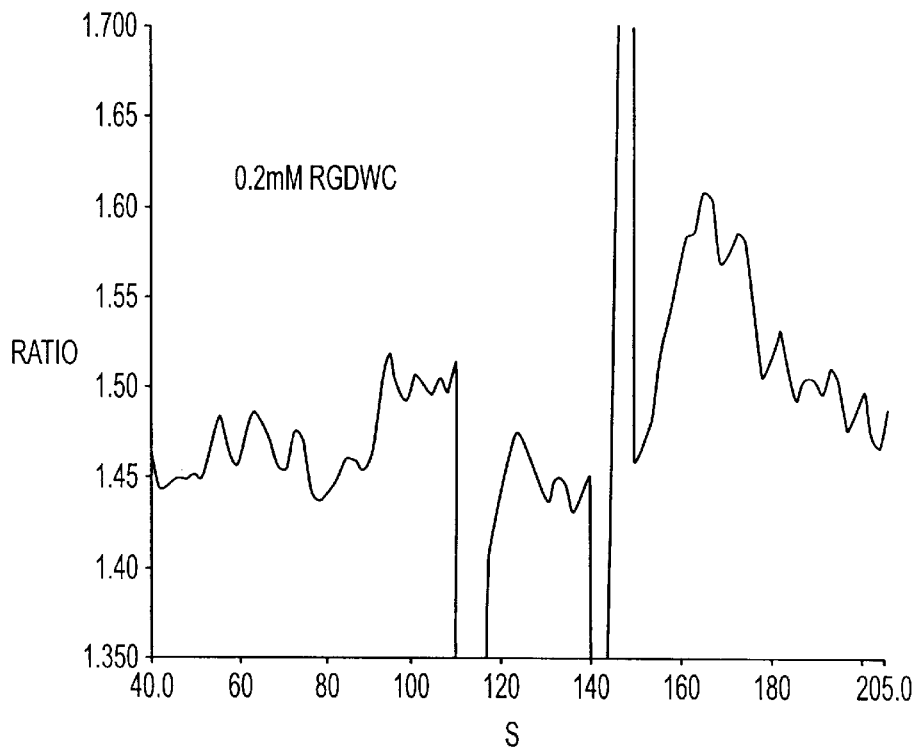
Figure 4C:
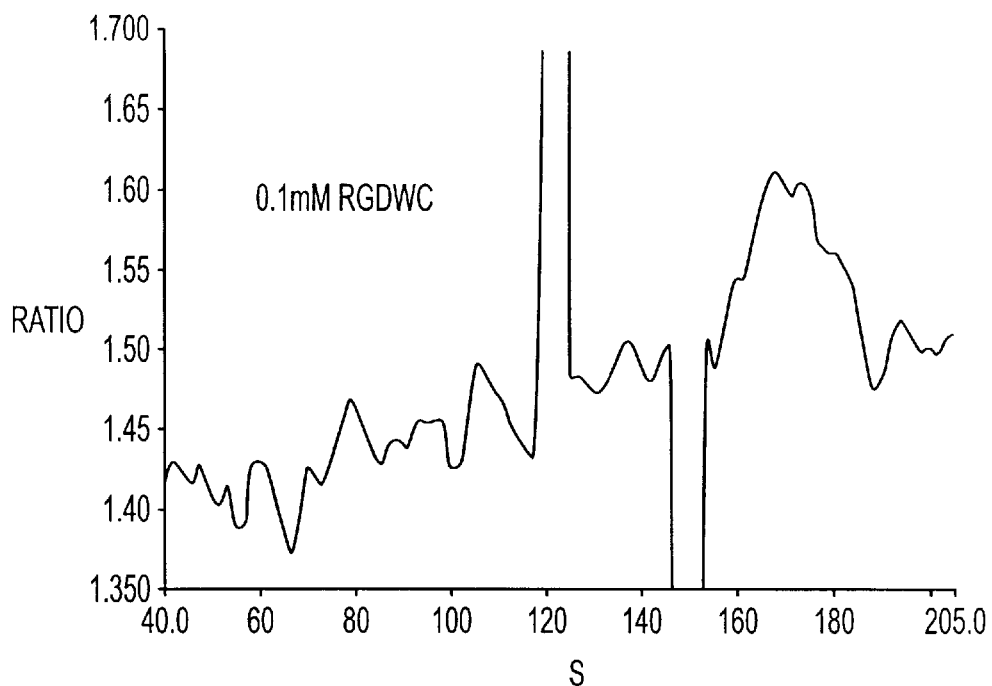
Figure 4D:
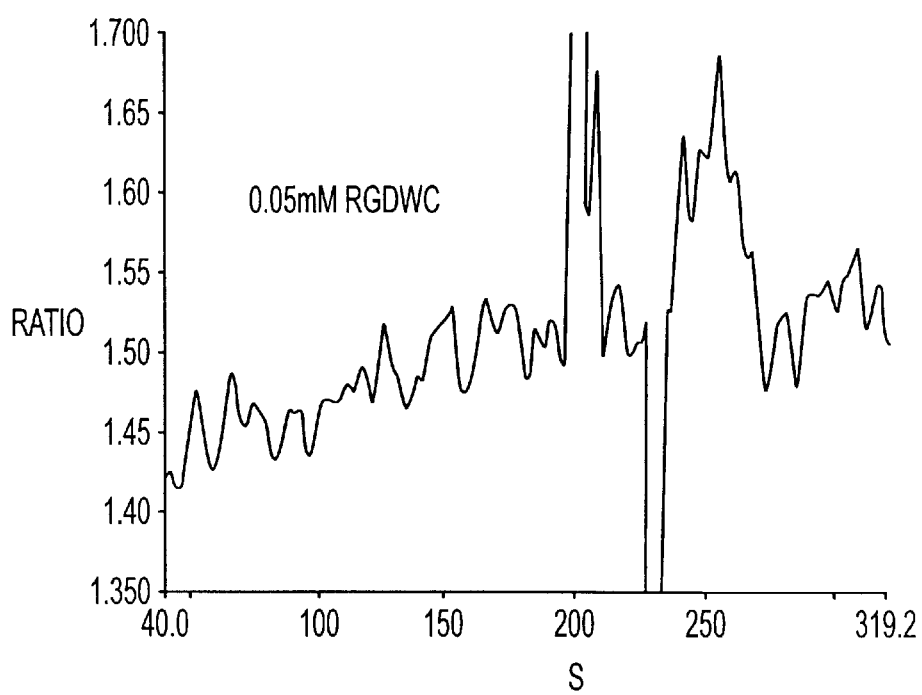
Figure 6:
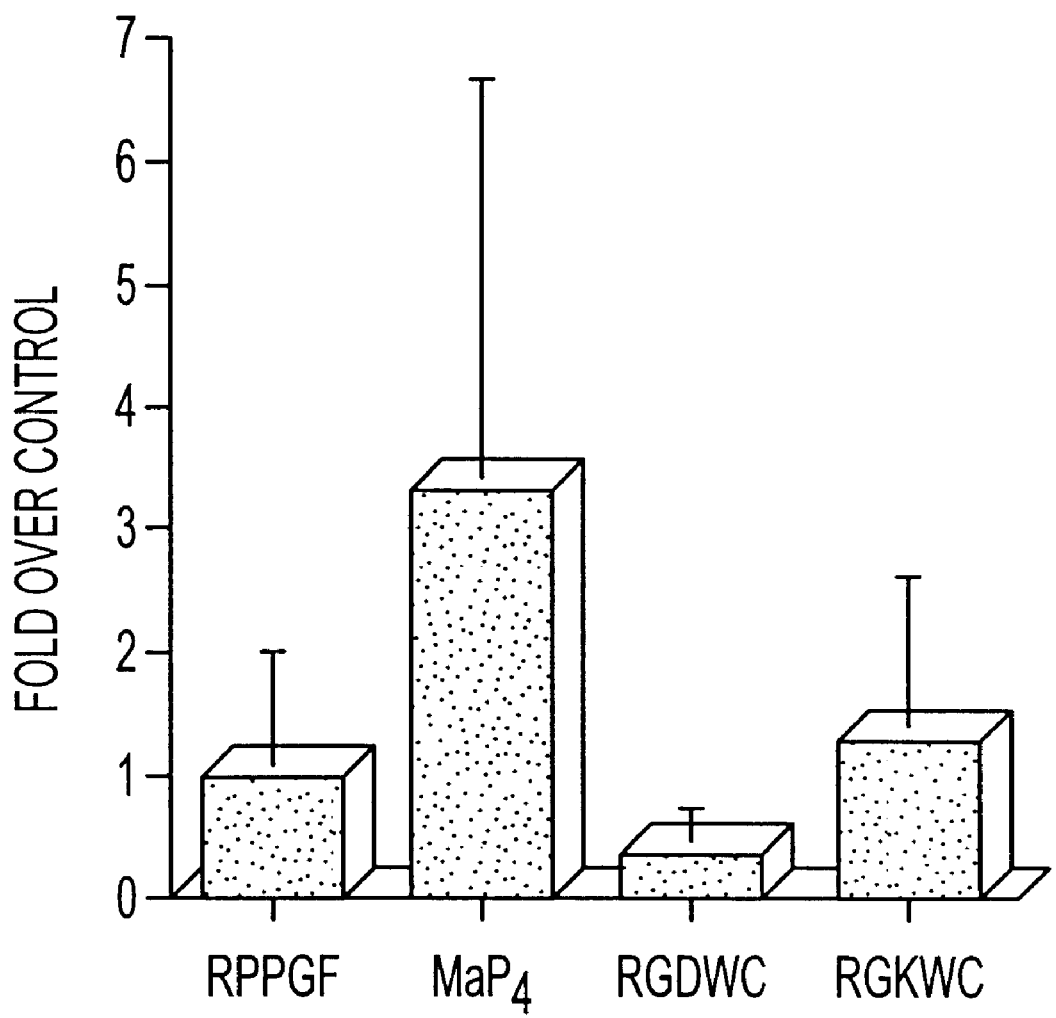
FIG. 6 examines the ability of biotinylated-peptide NATLDPRSFLLR (biotin-NAT12, SEQ ID NO: 41) binding to peptides RPPGF (Arg-Pro-Pro-Gly-Pro, SEQ ID NO: 39), MAP4RPPGF, RGDWC (Arg-Gly-Asp-Trp-Cys, (SEQ ID NO: 20), or RGKWC (Arg-Gly-Lys-Trp-Cys, SEQ ID NO: 5). Each of these peptides at 10 μg/ml was coupled to a microtiter plate by incubating them in 0.1 M $Na_2CO_3$, pH 9.6 buffer. Biotin-NAT12 was incubated with the plate and the level of bound biotinylated peptide was determined.

The second assay developed to assess peptides from the combinatorial libraries uses inhibition of α-thrombin-induced calcium mobilization in fibroblasts. Normal human lung fibroblasts (NHLF) were purchased from Clonetics, San Diego, Calif., an affiliate of Bio-Wittaker, Walkersville, Md. The cytoplasmic free Ca$^{2+}$ concentration ([Ca$^{2+}$]$_i$) was measured using the fluorescent Ca$^{2+}$ indicator fura-2 (Molecular Probes, Inc., Eugene, Oreg.). Suspension of fibroblasts in Hepes-Tyrode's buffer were loaded with fura-2 by incubation at 37° C. with 2 μM fura-2/acetoxymethyl ester for 45 minutes according to the method of Rasmussen et al., *J. Biol. Chem.* 268, 14322 (1993). The labeled fibroblasts were separated from excess probe by washing by centrifugation at 1000 rpm (180×g). Aliquots of the labeled fibroblasts were transferred into a quartz cuvette with a magnetic stirrer, which was then placed in a thennostatically controlled chamber at 37° C. in a fluorescence spectrophotometer (Perkin-Elmer LS50B spectrofluorometer, Chicago, Ill.). Reagents, test peptide (SEQ ID NO: 5) (from 0.2 mM to effective lower concentration), and α-thrombin (2–4 nM), were sequentially added directly to the cuvette. The excitation wavelengths varied between 340 and 380 nm. Fluorescence was measured by recording emitted light at 510 nm as reported by Fisher et al., *Mol Pharm.* 35, 195 (1989). The minimum emission was determined on a solubilized fibroblast sample in the presence of 10 mM EDTA; maximum emission was determined on the same sample with 10 mM Ca$^{2+}$ added. The intrafibroblast free Ca$^{2+}$ concentration was calculated by the method of Grykiewicz et al., *J. Biol. Chem.* 260, 3440 (1985). The ratio of the fluorescence readings was calculated as R=340/380 nm and processed according to the equation [Ca$^{2+}$]$_i$=K$_D$((R−R$_{min}$)/(R$_{max}$−R)) (S$_{f2}$/S$_{b2}$) to determine the intrafibroblast free Ca$^{2+}$ concentration. The KD for fura-2 was assumed to be 224 nM. R$_{max}$ and R$_{min}$ are the maximum and minimum fluorescence ratios measured at the end of the experiment, respectively; S$_{f2}$ and S$_{b2}$ are the fluorescence values at 380 nm in the absence and presence of saturating [Ca 2+], respectively. The reaction was monitored for 3–5 minutes. As shown in FIG. 2, peptide (SEQ ID NO: 5) RGKWC blocked 2 nM α-thrombin-induced $Ca^{2+}$ mobilization in fibroblasts at concentrations≧50 μM. Table II lists all the $RGKO_4C$ (SEQ ID NO: 43) peptides from the most potent to the least potent inhibitor of thrombin-induced $Ca^{2+}$ mobilization. The table shows, in decreasing potency, the percent inhibition of thrombin-induced calcium mobilization using 0.2 mM of each of the peptides. The eight most potent inhibitors in decreasing order were RGKWC, RGKKC, RGKRC, RGKHC, RGKPC, RGKQC, RGKTC, and RGKDC (SEQ ID NOS 5, 14, 3, 13, 16, 17, 2 & 9, respectively). In FIG. 4, peptide RGDWC (SEQ ID NO: 20) at 0.2 mM inhibited 31% of 4 nM α-thrombin-induced $Ca^{2+}$ mobilization in fibroblasts. Table V shows the list of $RGDO_4C$ (SEQ ID NO: 44) peptides from the most potent to least potent inhibitors of thrombin-induced $Ca^{2+}$ mobilization. The table shows, in decreasing potency, the percentage of inhibition of thrombin-induced calcium mobilization using 0.2 mM of each of the peptides. The seven most potent peptides in decreasing order of potency include: RGDNC, RGDWC, RGDFC, RGDKC, RGDMC, RGDYC, and RGDAC (SEQ ID NOS 32,20,21,29,24,35 and 37, respectively).

3. Biotin-NAT12 Binding Assay to Peptide Analoes

A third assay was developed to ascertain the ability of biotin-NAT12 (NATLDPRSFLLR, SEQ ID NO: 41) to directly bind to peptides linked to microtiter plates. In this assay, peptide analogs were linked to microtiter plate cuvette wells by incubation of the peptide in 0.1 M $Na_2CO_3$, pH 9.6 buffer overnight at 4° C. After coupling the peptide to the cuvette well, the wells were dumped and each well was blocked with 1% bovine serun albumin in 0.01 M $Na_3PO_4$, 0.15 M NaCl, at pH 7.4. After incubation for 1 hour, the wells were dumped and washed three times with PBS-Tween. The wells were then incubated with biotin-NAT12. The amount of biotin-NAT12 bound was determined by adding streptavidin-peroxidase followed by adding turbo TMB (Pierce).

FIG. 5 shows that peptide RGKWC (SEQ ID NO: 5) binds to a greater extent than peptide RGDWC (SEQ ID NO: 20). The level of binding of (SEQ ID NO: 5) RGKWC was greater than RPPGF (SEQ ID NO: 39). However, its level of binding was less than that seen with the multiple branched peptide MAP4RPPGF. Table III shows the $RGKO_4C$ (SEQ ID NO: 43) peptides that bind biotin-NAT12. In decreasing order of binding level, these peptides include: RGKSC, RGKMC, RGKHC, RGKKC, RGKFC, RGKLC, RGKWC, and RGKVC (SEQ ID NOS 18, 7, 13, 14, 11, 1, 5 and 19, respectively). Table VI shows the $RGDO_4C$ (SEQ ID NO: 44) peptides that bind biotin-NAT12. The best $RGDO_4C$ (SEQ ID NO: 44) peptide (RGDSC, SEQ ID NO: 34) to bind biotin-NAT12 was equivalent to the ability of RGKWC (SEQ ID NO: 5) to bind biotin-NAT12. The best to least $RGDO_4C$ (SEQ ID NO: 44) peptides to bind biotin-NAT12 listed in Table VI are: RGDSC, RGDGC, RGDQC, RGDEC, RGDIC, RGDPC, RGDDC, and RGDYC (SEQ ID NOS 34, 28, 23, 22, 36, 38, 27 and 35, respectively). A solid phase peptide-peptide binding assay was used to determine biotin-NAT12 binding to library peptides. Test peptides in 0.1 M $Na_2CO_3$, pH 9.6 buffer, at 10 μg/well in 50 μl volume, were coupled to microtiter plate wells by overnight incubation at 4° C. After incubation, the contents of the wells were discarded and the wells were washed with a pH 7.4 buffer containing 0.01 M $Na_3PO_4$, 0.15 M NaCl, and 0.01% Tween 20. After blocking each well with 1% radioimmunoassay grade bovine serum albumin, the linked peptides were incubated with 100 μl of 100 μM biotin-NAT12 for 1 hour at 37° C. After incubation, the contents of the wells were dumped and the wells were washed three times (100 μl/well each time) with the buffer identified above. Each well then was incubated with 100 μl of 2 μg/ml solution of Immuno-Pure streptoavidin horeseradish peroxidase conjugate (Pierce Chemical Co., Rockville, Ill.) for 1 hour at room temperature. The contents of the wells were discarded and the wells were washed three times as described above. The wells were then incubated with 100 μl of peroxidase-specific fast reacting substrate, turbo-3,3',5,5'-tetramethylbenzidine (turbo-TMB, Pierce) for 5 minutes at room temperature and the developing color reaction was stopped by the addition of 100 μof 1 M phosphoric acid. The absorbance was measured at 450 nm using a Microplate Auto Reader EL311 (Bio-Tek, Winooski, Vt.). The extent of biotin-NAT12 binding to test peptides from the libraries was assessed by the degree of absorbance displayed.

B. Preparation of Peptide Combinatorial Library

Three successive combinatorial libraries were prepared to obtain the peptide analogs that are contained herein. The first library started with the peptide RPPGF (Arg-Pro-Pro-Gly-Phe, SEQ ID NO: 39). Investigations showed that an alanine substitution in the peptide at position 1 at the amino terminal end resulted in marked loss of thrombin inhibitory activity. Alternatively, substitution in the fifth position at the carboxyterminal end of a cysteine for a phenylalanine did not result in any loss of activity. Since cysteine in this fifth position promoted binding of the peptides to plastic plates, all subsequent peptides had cysteine placed at this position.

The initial positional peptide combinatorial library consisted of $H-RO_2XXC-NH_2$ (SEQ If) NO: 43), $H-RXO_3XC-NH_2$, and $H-RXXO_4C-NH_2$, where $O_2$, $O_3$, or $O_4$ represents all L-amino acids from A to Y, except cysteine, and X is an equimolar mixture of L-amino acids from A to Y, except cysteine (Houghten et al., *BioTechniques* 13(3): 412–421 (1992)). Investigations revealed that a glycine in the second position produced a peptide(s) with the best ability to inhibit thrombin-induced platelet aggregation, to inhibit thrombin-induced calcium mobilization, and to bind biotin-NAT12. A second peptide combinatorial library was designed to examine the third and fourth position of this sequence. Peptides $H-RGO_3XC-NH_2$ and $H-RGXO_4C-NH_2$ were prepared where $O_3$ and $O_4$ were all L-amino acids from A to Y, except cysteine, and X was an equimolar mixture of L-amino acids from A to Y, except cysteine. Investigations revealed that a lysine or aspartic acid in the third position produced peptides with the best ability to inhibit thrombin-induced platelet aggregation, inhibit thrombin-induced calcium mobilization, and bind biotin-NAT12. A third library was prepared where the third positions were fixed as a lysine or aspartic acid: $H-RGKO_4C-NH_2$ and $H-RGDO_4C-NH_2$ (SEQ ID NOS: 43 and 44, respectively), where $O_4$ is all L-amino acids except cysteine. The peptides from this third combinatorial library are the peptide analogs being described herein.

A standard solid phase automated peptide synthesis was utilized to prepare the peptide libraries. The synthetic peptide libraries were prepared using methylbenzhydrylamine (MBHA) polystyrene resin and standard t-Boc chemistry in combination with simultaneous multiple peptide synthesis (SMPS) (Houghten et al., *Nature*. 354, 84–86 (1991); Houghten et al., *BioTechniques*. 13, 412–421 (1992); Dooley et al., *Science*. 266, 2019–2022 (1994)). A peptide synthesis resin was prepared that assures equimolarity of the peptides on the resin (Houghten et al., *BioTechniques*. 13, 412–421 (1992)). Nineteen porous polypropylene packets, each containing 4.65 mmol of MBHA resin, were coupled to each of the protected N-α-t-Boc amino acids of interest (Houghten et al., *BioTechniques*. 13, 412–421 (1992)). Cysteine was excluded from the coupling mixture. In all cases the coupling reactions were >99.9% complete as assessed by picric acid or ninhydrin tests (Gisin *Analytica chim. Acta*.

58, 248–249, (1972); Kaiser et al., *Analyt. Biochem.* 34, 595–598 (1970)). The resulting resins from each packet were combined and thoroughly mixed. There were approximately 4000 beads per mg of resin. The resin mixture was then separated into 19 portions of equal weight which were then placed into porous polypropylene packets, followed by N-α-t-Boc protecting group removal and neutralization of the resulting amine TFA salts. The resin packets were then reacted with solutions of the individual activated amino acids to yield the various peptide combinations. The peptide mixtures were deprotected and then cleaved from their respective resins using low-high hydrogen fluoride (HF) (Cuervo et al., *Peptide Res.* 1, 81–86 (1991); Tam, J.P., et al., *J. Am. Chem. Soc.* 105, 6442–6455 (1983); Houghten et al., *Int. J. Peptide Protein Res.* 27, 673–678 (1986)) in a multiple HF cleavage apparatus (Multiple Peptide Systems, San Diego, Calif.). Extraction of the individual peptide mixtures was carried out with $H_2O$ or dilute acetic acid and the solutions lyophilized.

TABLE I

Effect of (SEQ ID NO: 43) $RGKO_4C$ Peptide Sublibrary on Thrombin-Induced Platelet Aggregation

| Peptide | Fold Increase in Aggregation Inhibition over (SEQ ID NO: 39) RPPGF | SD |
| --- | --- | --- |
| RGKLC (SEQ ID NO: 1) | 7.7 | 7.2 |
| RGKTC (SEQ ID NO: 2) | 4.4 | 4.4 |
| RGKRC (SEQ ID NO: 3) | 2.5 | |
| RGKIC (SEQ ID NO: 4) | 1.3 | |
| RGKWC (SEQ ID NO: 5) | 1.3 | 0.4 |
| RGKYC (SEQ ID NO: 6) | 1.3 | |
| RGKMC (SEQ ID NO: 7) | 1.3 | |
| RGKAC (SEQ ID NO: 8) | | |
| RGKDC (SEQ ID NO: 9) | | |
| RGKEC (SEQ ID NO: 10) | | |
| RGKFC (SEQ ID NO: 11) | | |
| RGKGC (SEQ ID NO: 12) | | |
| RGKHC (SEQ ID NO: 13) | | |
| RGKKC (SEQ ID NO: 14) | | |
| RGKNC (SEQ ID NO: 15) | | |
| RGKPC (SEQ ID NO: 16) | | |
| RGKQC (SEQ ID NO: 17) | | |
| RGKSC (SEQ ID NO: 18) | | |
| RGKVC (SEQ ID NO: 19) | | |
| RPPGF (SEQ ID NO: 39) | 1.0 | |

TABLE II

Inhibition of Thrombin-Induced Calcium Mobilization by Peptides of the (SEQ ID NO: 43) $RGKO_4C$ Peptide Sublibrary

| Peptide | $Ca^{2+}$ % Inhibition At 0.2 mM Peptide | SD |
| --- | --- | --- |
| RGKWC (SEQ ID NO: 5) | 62.5 | 18.75 |
| RGKKC (SEQ ID NO: 14) | 38.9 | 13.7 |
| RGKRC (SEQ ID NO: 3) | 35.7 | |
| RGKHC (SEQ ID NO: 13) | 31.2 | 2.84 |
| RGKPC (SEQ ID NO: 16) | 31.13 | 23.7 |
| RGKQC (SEQ ID NO: 17) | 28 | 6.5 |
| RGKTC (SEQ ID NO: 2) | 26.8 | 37.9 |
| RGKDC (SEQ ID NO: 9) | 26.7 | 37.7 |
| RGKVC (SEQ ID NO: 19) | 17.3 | |
| RGKEC (SEQ ID NO: 10) | 13.8 | 19.5 |
| RGKIC (SEQ ID NO: 4) | 13.8 | 8.67 |
| RGKGC (SEQ ID NO: 12) | 12.4 | 4.24 |
| RGKLC (SEQ ID NO: 1) | 8.33 | 11.78 |
| RGKMC (SEQ ID NO: 7) | 7.95 | 11.25 |
| RGKAC (SEQ ID NO: 8) | 5.2 | |
| RGKFC (SEQ ID NO: 11) | 2.74 | 3.88 |
| RGKSC (SEQ ID NO: 18) | 0.01 | |
| RGKNC (SEQ ID NO: 15) | 0 | |
| RGKYC (SEQ ID NO: 6) | 0 | |

TABLE III

Binding of Biotin-NAT12 Peptide from PAR1 to the (SEQ ID NO: 43) $RGKO_4C$ Peptide Sublibrary

| Peptide | Level of Binding to Biotin-NAT12 | SD |
| --- | --- | --- |
| RGKSC (SEQ ID NO: 18) | 2.2 | 1.5 |
| RGKMC (SEQ ID NO: 7) | 2.1 | 1.6 |
| RGKHC (SEQ ID NO: 13) | 2.1 | 0.7 |
| RGKKC (SEQ ID NO: 14) | 1.8 | 1.1 |
| RGKFC (SEQ ID NO: 11) | 1.5 | 1.1 |
| RGKLC (SEQ ID NO: 1) | 1.5 | 1.1 |
| RGKWC (SEQ ID NO: 5) | 1.3 | 1.4 |
| RGKVC (SEQ ID NO: 19) | 1.2 | 0.8 |
| RGKPC (SEQ ID NO: 16) | 1.2 | 0.8 |
| RGKNC (SEQ ID NO: 15) | 1.2 | 0.7 |
| RGKGC (SEQ ID NO: 12) | 1.0 | 0.5 |
| RGKIC (SEQ ID NO: 4) | 0.98 | 0.07 |
| RGKYC (SEQ ID NO: 6) | 0.94 | 0.64 |
| RGKEC (SEQ ID NO: 10) | 0.926 | 0.397 |
| RGKDC (SEQ ID NO: 9) | 0.82 | 0.36 |
| RGKAC (SEQ ID NO: 8) | 0.689 | 0.005 |
| RGKTC (SEQ ID NO: 2) | 0.597 | 0.609 |
| RGKRC (SEQ ID NO: 3) | 0.38 | 0.53 |
| RGKQC (SEQ ID NO: 17) | 0.374 | 0.152 |
| RPPGF (SEQ ID NO: 39) | 1.0 | |

TABLE IV

Effect of (SEQ ID NO: 44) $RGDO_4C$ Peptide Sublibrary on Thrombin-Induced Platelet Aggregation

| Peptide | Fold Increase in Aggregation Inhibition over (SEQ ID NO: 39) RPPGF | SD |
| --- | --- | --- |
| RGDWC (SEQ ID NO: 20) | 31.7 | 41.9 |
| RGDFC (SEQ ID NO: 21) | 25 | 7.1 |
| RGDEC (SEQ ID NO: 22) | 20 | |
| RGDQC (SEQ ID NO: 23) | 15.8 | 21 |
| RGDMC (SEQ ID NO: 24) | 15 | 7.1 |
| RGDVC (SEQ ID NO: 25) | 15 | 7.1 |
| RGDHC (SEQ ID NO: 26) | 14.8 | 14.1 |
| RGDDC (SEQ ID NO: 27) | 7.5 | |
| RGDGC (SEQ ID NO: 28) | 7.5 | |
| RGDKC (SEQ ID NO: 29) | 7.5 | 3.5 |
| RGDLC (SEQ ID NO: 30) | 7.5 | 3.5 |
| RGDTC (SEQ ID NO: 31) | 7.5 | 3.5 |
| RGDNC (SEQ ID NO: 32) | 5 | |
| RGDRC (SEQ ID NO: 33) | 5 | |
| RGDSC (SEQ ID NO: 34) | 5 | |
| RGDYC (SEQ ID NO: 35) | 5 | |
| RGDIC (SEQ ID NO: 36) | 3.8 | 1.8 |
| RGDA (SEQ ID NO: 37) | | |
| RGDPC (SEQ ID NO: 38) | | |
| RPPGF (SEQ ID NO: 39) | 1 | |

TABLE V

Inhibition of Thrombin-Induced Calcium Mobilization by Peptides of the (SEQ ID NO: 44) RGDO₄C Peptide Sublibrary

| Peptide | Ca²⁺ % Inhibition At 0.2 mM Peptide | SD |
|---|---|---|
| RGDNC (SEQ ID NO: 32) | 44.3 | 5.6 |
| RGDWC (SEQ ID NO: 20) | 31.9 | 4.6 |
| RGDFC (SEQ ID NO: 21) | 30.3 | 42.9 |
| RGDKC (SEQ ID NO: 29) | 28.1 | 16 |
| RGDMC (SEQ ID NO: 24) | 26.2 | 32.6 |
| RGDYC (SEQ ID NO: 35) | 16.4 | |
| RGDAC (SEQ ID NO: 37) | 11 | 4.7 |
| RGDGC (SEQ ID NO: 28) | 9.9 | 14 |
| RGDHC (SEQ ID NO: 26) | 9.9 | 14 |
| RGDIC (SEQ ID NO: 36) | 9.3 | 13.2 |
| RGDDC (SEQ ID NO: 27) | 8.9 | 12.6 |
| RGDQC (SEQ ID NO: 23) | 8.45 | 11.9 |
| RGDPC (SEQ ID NO: 38) | 4.13 | 5.85 |
| RGDVC (SEQ ID NO: 25) | 2.56 | 3.63 |
| RGDEC (SEQ ID NO: 22) | 1.96 | 2.77 |
| RGDLC (SEQ ID NO: 30) | 0 | |
| RGDRC (SEQ ID NO: 33) | 0 | |
| RGDSC (SEQ ID NO: 34) | 0 | |
| RGDTC (SEQ ID NO: 31) | 0 | |

TABLE VI

Binding of Biotin-NAT12 Peptide from PAR1 to the (SEQ ID NO: 44) RGDO₄C Peptide Sublibrary

| Peptide | Level of Binding to Biotin-NAT12 | SD |
|---|---|---|
| RGDSC (SEQ ID NO: 34) | 1.44 | 0.3 |
| RGDGC (SEQ ID NO: 28) | 1.39 | 0.08 |
| RGDQC (SEQ ID NO: 23) | 1.32 | 0.16 |
| RGDEC (SEQ ID NO: 22) | 1.28 | 0.08 |
| RGDIC (SEQ ID NO: 36) | 1.22 | 0.61 |
| RGDPC (SEQ ID NO: 38) | 1.12 | 0.12 |
| RGDDC (SEQ ID NO: 27) | 1.11 | 0.3 |
| RGDYC (SEQ ID NO: 35) | 1.05 | 0.089 |
| RGDRC (SEQ ID NO: 33) | 0.99 | 0.4 |
| RGDLC (SEQ ID NO: 30) | 0.98 | 0.19 |
| RGDMC (SEQ ID NO: 24) | 0.87 | 0.27 |
| RGDAC (SEQ ID NO: 37) | 0.8 | 0.26 |
| RGDHC (SEQ ID NO: 26) | 0.759 | 0.356 |
| RGDTC (SEQ ID NO: 31) | 0.746 | 0.175 |
| RGDNC (SEQ ID NO: 32) | 0.739 | 0.081 |
| RGDVC (SEQ ID NO: 25) | 0.723 | 0.189 |
| RGDFC (SEQ ID NO: 21) | 0.671 | 0.101 |
| RGDKC (SEQ ID NO: 29) | 0.67 | 0.041 |
| RGDWC (SEQ ID NO: 20) | 0.374 | 0.008 |
| RPPGF (SEQ ID NO: 39) | 1 | |

TABLE VII

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention is intended for use in individuals with acute coronary syndromes (crescendo angina, myocardial infarction) and in individuals who have acute coronary syndromes and receive percutaneous transluminal coronary angioplasty (PTCA) with an artificial stent placement. The present invention can be used as a single agent alone or in combinations with other agents. These other agents may include any one or number of the following drugs (including all of them): standard heparin, low molecular weight heparin, aspirin, ticlopidine, clopidogrel, abciximab, tirofiban, or eptifibatide. The compounds of the present invention may be administered intravenously with the other agent(s) to treat individuals for acute coronary syndromes and during the related management. This invention also could be useful in the management of individuals with dacron grafts from peripheral bypass surgery and individuals with stents for carotid or renal artery stenosis. Agents such as those being presented here may be useful in the management of patients with transient ischemic attacks, stroke in progression, and complete stroke in the brain.

Purified peptides of the invention may be administered under circumstances where inhibition of thrombin-induced platelet activation or platelet aggregation is sought. The analogs are for use and administration to subjects experiencing platelet thrombosis from any cause, and may be used prophylactically in surgery or catheterization for insertion of artificial dacron grafts and stents to prevent reocclusion events due to platelet thrombi. Thus, the analogs may be infused into individuals to prevent strokes and cerebral edema.

The analogs may be administered by any convenient means, which will result in substantial delivery into the blood stream. Preferably the administration is parenterally. However, the administration of analogs can be executed by any means which will introduce the analogs into the bloodstream, including intravenous, intranasal, and oral administration, as well as administration via a dermal patch or rectal suppositories. Intravenous administration is presently contemplated as the preferred administration route, although intranasal administration may also be utilized.

The peptide analogs may be combined with any pharmaceutical carrier, which is physiologically acceptable to the host. The pharmaceutical composition may be compounded according to conventional pharmaceutical techniques. The carrier may be provided in a variety of forms depending on the form of preparation desired for administration. For parenteral administration, the carrier can comprise sterile water, and optionally other ingredients to aid solubility or preservative purposes. In intravenous administration, the preferred parenteral route, the analogs may be dissolved in appropriate intravenous delivery vehicles containing physiologically compatible substances, such as sterile sodium chloride having a buffered pH compatible with physiologic conditions, e.g. saline. Injectable suspension may also be prepared, in which case appropriate liquid carriers, suspending agents and the like may be employed.

The dosage of administration will depend on the size and weight of the patient. Those skilled in the art of infusion therapy in ICU or in interventional cardiology can derive appropriate dosages and schedules of administration to suit the specific circumstances and needs of the patient. The physiologically acceptable dosages range from about 10 to 30 mg per day per kg of body weight. In preferred intravenous administration, the dosage is 10 mg/kg body weight in 5 ml of normal saline or in any suitable vehicle given at a rate of 1 ml/min. The therapeutically optimal amounts of dosage may be determined by monitoring pre- and post-infusion platelet function by determining ex vivo γ-thrombin induced platelet aggregation and secretion, and also by measuring hemostatic parameters like activated partial thromboplastin time (APTT), prothombin time (PT), thrombin time (TT), and template bleeding time (BT).

We claim:

1. A method for inhibiting thrombin induced platelet aggregation in a human cell expressing Protease Activated Receptor 1 (PAR1), comprising:
providing a mixture comprising thrombin and a human cell expressing PAR1, wherein the concentration of thrombin is effective to induce stimulus-response coupling within the cell;
contacting the mixture with a compound comprising at least one segment having an amino acid sequence selected from the group consisting of Formula I and Formula II,
wherein Formula I is Arg-Gly-Lys-$Z_4$-Cys (SEQ ID NO: 43)

wherein $Z_4$ is any naturally occurring amino acid, excluding cysteine; and
wherein Formula II is Arg-Gly-Asp-$Z_4$-Cys (SEQ ID NO: 44)

wherein $Z_4$ is any naturally occurring amino acid, excluding cysteine; and
wherein said compound contains at most 10 amino acids in said segment and thereby inhibiting thrombin induced platelet aggregation.

2. The method of claim 1, which thrombin is selected from the group consisting of alpha thrombin, gamma thrombin, and admixtures thereof.

3. The method of claim 1, which comprises inhibiting thrombin induced platelet aggregation wherein said thrombin is selected from the group consisting of alpha-thrombin and gamma-thrombin.

4. The method of claim 3, wherein said segment is

Arg-Gly-Lys-Trp-Cys (SEQ ID NO: 5).

5. The method of claim 3, wherein said segment is

Arg-Gly-Asp-Trp-Cys (SEQ ID NO: 20).

6. The method of claim 1, which comprises inhibiting thrombin induced calcium mobilization in fibroblasts.

7. The method of claim 6, wherein said segment is

Arg-Gly-Lys-Trp-Cys (SEQ ID NO: 5).

8. The method of claim 6, wherein said segment is

Arg-Gly-Asp-Trp-Cys (SEQ ID NO: 20).

9. The method of claim 1, wherein said compound comprises at most 5 amino acids in sequence.

10. The method of claim 1, wherein said cell expressing PAR1 is selected from the group consisting of platelets, endothelial cells, brain cells, fibroblasts, and smooth muscle cells.

11. A method of binding a compound to biotinylated-peptide Asn-Ala-Thr-Leu-Asp-Pro-Arg-Ser-Phe-Leu-Leu-Arg (SEQ ID NO: 41) (biotin-NAT12) comprising:
providing a compound comprising at least one segment having an amino acid sequence selected from the group consisting of Formnula I and Formula II,
wherein Formula I is Arg-Gly-Lys-$Z_4$-Cys (SEQ ID NO: 43)

wherein $Z_4$ is any naturally occurring amino acid, excluding cysteine; and
wherein Formula II is Arg-Gly-Asp-$Z_4$-Cys (SEQ ID NO: 44)

wherein $Z_4$ is any naturally occurring amino acid, excluding cysteine;
wherein said compound contains at most 10 amino acids in said segment; and
incubating biotinylated-peptide Asn-Ala-Thr-Leu-Asp-Pro-Arg-Ser-Phe-Leu-Leu-Arg (SEQ ID NO: 41) (biotin-NAT12) with said compound and thereby binding said compound to said biotin-NAT12.

12. The method of claim 11, wherein said segment is

Arg-Gly-Lys-Trp-Cys (SEQ ID NO: 5).

13. A method for inhibiting thrombin activation in a sample comprising blood platelets, comprising:

providing a solution comprising thrombin and blood platelets, wherein the concentration of thrombin is effective to cause platelet aggregation;

contacting the blood sample with a compound comprising at least one segment having an amino acid sequence selected from the group consisting of Formula I and Formula II, wherein Formula I is Arg-Gly-Lys-$Z_4$-Cys (SEQ ID NO: 43)

wherein $Z_4$ is any naturally occurring amino acid, excluding cysteine; and wherein Formula II is Arg-Gly-Asp-$Z_4$-Cys (SEQ ID NO: 44)

wherein $Z_4$ is any naturally occurring amino acid, excluding cysteine; and wherein said compound contains at most 10 amino acids in said segment and thereby inhibiting thrombin activation in said sample.

14. The method of claim 13 wherein thrombin is selected from the group consisting of alpha-thrombin, gamma-thrombin, and admixtures thereof.

15. The method of claim 13, which comprises inhibiting thrombin induced platelet aggregation wherein said thrombin is selected from the group consisting of alpha-thrombin and gamma-thrombin.

16. The method of claim 15, wherein said segment is

Arg-Gly-Lys-Trp-Cys (SEQ ID NO: 5).

17. The method of claim 15, wherein said segment is

Arg-Gly-Asp-Trp-Cys (SEQ ID NO: 20).

18. The method of claim 13, wherein said compound comprises at most 5 amino acids in sequence.

19. A compound comprising at least one segment with an amino acid sequence of a formulae selected from the group consisting of Formula I and Formula II wherein Formula I is Arg-Gly-Lys-$Z_4$-Cys (SEQ ID NO: 43)

wherein $Z_4$ is any naturally occurring amino acid, excluding cysteine or asparagine; and wherein Formula II is Arg-Gly-Asp-$Z_4$-Cys (SEQ ID NO: 44)

wherein $Z_4$ is any naturally occurring amino acid, excluding cysteine; and wherein the compound contains at most 10 amino acids in sequence.

20. The compound of claim 19, wherein the segment of Formula I is

Arg-Gly-Lys-Trp-Cys (SEQ ID NO: 5)

and wherein the segment of Formula II is

Arg-Gly-Asp-Trp-Cys (SEQ ID NO: 20).

21. The compound of claim 19, wherein the segment Formula I is

Arg-Gly-Lys-Trp-Cys (SEQ ID NO: 5)

and wherein the segment of Formula II is

Arg-Gly-Asp-Trp-Cys (SEQ ID NO: 20).

22. The compound of claim 19, wherein the segment of Formula I is

Arg-Gly-Lys-Trp-Cys (SEQ ID NO: 5).

23. The compound of claim 19, wherein the compound comprises at most 5 amino acids in sequence.

24. The method of claim 6, wherein the segment is Arg-Gly-Lys-Trp-Cys (SEQ ID NO: 5).

25. The method of claim 15, wherein the segment is Arg-Gly-Lys-Trp-Cys (SEQ ID NO: 20).

26. A method of preventing thrombosis, wherein thrombosis is defined as occlusion of a vessel due to formation of a platelet-rich, fibrin-rich, or a mixed platelet-fibrin thrombus, wherein the method comprises the method of claim 1, thereby preventing thrombosis.

27. The compound of claim 19, wherein the segment is Arg-Gly-Lys-Trp-Cys (SEQ ID NO: 5).

28. The compound of claim wherein the segment is Arg-Gly-Asp-Trp-Cys (SEQ ID NO: 20).

29. The method of claim 1 wherein the compound comprises at least one segment having an amino acid sequence of Formula I.

30. The method of claim 1 wherein the compound comprises at least one segment having an amino acid sequence of Formula II.

31. The method of claim 9 wherein said compound is

Arg-Gly-Lys-Trp-Cys (SEQ ID NO: 5).

32. The method of claim 9 wherein said compound is

Arg-Gly-Asp-Trp-Cys (SEQ ID NO: 20).

33. The method of claim 9 wherein said compound is selected from the group consisting of Arg-Gly-Lys-Ile-Cys (SEQ ID NO: 5); and Arg-Gly-Lys-Trp-Cys (SEQ ID NO: 20).

* * * * *

SEQUENCE LISTING

```
<160> NUMBER OF SEQ ID NOS: 46

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Arg Gly Lys Leu Cys
 1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 2

Arg Gly Lys Thr Cys
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 3

Arg Gly Lys Arg Cys
 1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 4

Arg Gly Lys Ile Cys
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 5
```

Arg Gly Lys Trp Cys
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 6

Arg Gly Lys Tyr Cys
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 7

Arg Gly Lys Met Cys
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 8

Arg Gly Lys Ala Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 9

Arg Gly Lys Asp Cys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 10

Arg Gly Lys Glu Cys
1               5

<210> SEQ ID NO 11
<211> LENGTH: 5
<212> TYPE: PRT
<213> ORGANISM: Artificial Sequence

```
<220> FEATURE:
<223> OTHER INFORMATION: Description of Artificial Sequence: synthetic
      peptide

<400> SEQUENCE: 11

Arg Gly Lys Phe Cys
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 12

Arg Gly Lys Gly Cys
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 13

Arg Gly Lys His Cys
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 14

Arg Gly Lys Lys Cys
 1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 15

Arg Gly Lys Asn Cys
 1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 16

Arg Gly Lys Pro Cys
 1               5
```

```
<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 17

Arg Gly Lys Gln Cys
  1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 18

Arg Gly Lys Ser Cys
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 19

Arg Gly Lys Val Cys
  1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 20

Arg Gly Asp Trp Cys
  1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 21

Arg Gly Asp Phe Cys
  1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 22

Arg Gly Asp Glu Cys
 1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 23

Arg Gly Asp Gln Cys
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 24

Arg Gly Asp Met Cys
 1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 25

Arg Gly Asp Val Cys
 1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 26

Arg Gly Asp His Cys
 1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 27

Arg Gly Asp Asp Cys
 1               5

<210> SEQ ID NO 28
<211> LENGTH: 5
<212> TYPE: PRT
```

```
<213> ORGANISM: Artificial Sequence
<220> FEATURE:
<223> OTHER INFORMATION: Description of Artificial Sequence: synthetic
      peptide

<400> SEQUENCE: 28

Arg Gly Asp Gly Cys
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 29

Arg Gly Asp Lys Cys
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 30

Arg Gly Asp Leu Cys
 1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 31

Arg Gly Asp Thr Cys
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 32

Arg Gly Asp Asn Cys
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 33

Arg Gly Asp Arg Cys
 1               5
```

```
<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 34

Arg Gly Asp Ser Cys
 1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 35

Arg Gly Asp Tyr Cys
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 36

Arg Gly Asp Ile Cys
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 37

Arg Gly Asp Ala Cys
 1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 38

Arg Gly Asp Pro Cys
 1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: synthetic
      peptide
```

```
<400> SEQUENCE: 39

Arg Pro Pro Gly Phe
 1               5

<210> SEQ ID NO 40
<211> LENGTH: 9
<212> TYPE: PRT
<213> ORGANISM: Homo sapiens

<400> SEQUENCE: 40

Arg Pro Pro Gly Phe Ser Pro Phe Arg
 1               5

<210> SEQ ID NO 41
<211> LENGTH: 12
<212> TYPE: PRT
<213> ORGANISM: Homo sapiens

<400> SEQUENCE: 41

Asn Ala Thr Leu Asp Pro Arg Ser Phe Leu Leu Arg
 1               5                  10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<223> OTHER INFORMATION: Xaa at position 4 may be any naturally
      occurring amino acid excluding Arg and Cys

<400> SEQUENCE: 42

Arg Gly Lys Xaa Cys
 1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<223> OTHER INFORMATION: Xaa at position 4 may be any naturally
      occurring amino acid excluding Cys

<400> SEQUENCE: 43

Arg Gly Lys Xaa Cys
 1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: synthetic
      peptide formula
<220> FEATURE:
<223> OTHER INFORMATION: Xaa at position 4 may be any naturally
      occurring amino acid excluding Cys

<400> SEQUENCE: 44

Arg Gly Asp Xaa Cys
 1               5
```

-continued

```
<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 45

Arg Pro Pro Gly
  1

<210> SEQ ID NO 46
<211> LENGTH: 6
<212> TYPE: PRT
<213> ORGANISM: Homo sapiens

<400> SEQUENCE: 46

Ser Phe Leu Leu Arg Asn
  1               5
```